United States Patent
Schapiro et al.

(10) Patent No.: US 10,843,994 B2
(45) Date of Patent: Nov. 24, 2020

(54) RECOVERY OF OXALIC ACID FROM INDUSTRIAL FERROUS OXALATE

(71) Applicant: TAL OR ECOLOGY LTD., Rehovot (IL)

(72) Inventors: Reuben David Schapiro, Rehovot (IL); Vladimir Boiko, Rehovot (IL); Lev Shapiro, Beer Sheva (IL)

(73) Assignee: TAL OR ECOLOGY LTD., Rehovot (IL)

( * ) Notice: Subject to any disclaimer, the term of this patent is extended or adjusted under 35 U.S.C. 154(b) by 0 days.

(21) Appl. No.: 16/330,576

(22) PCT Filed: Sep. 11, 2017

(86) PCT No.: PCT/IL2017/051021
§ 371 (c)(1),
(2) Date: Mar. 5, 2019

(87) PCT Pub. No.: WO2018/047184
PCT Pub. Date: Mar. 15, 2018

(65) Prior Publication Data
US 2019/0359549 A1      Nov. 28, 2019

Related U.S. Application Data

(60) Provisional application No. 62/393,153, filed on Sep. 12, 2016.

(51) Int. Cl.
*C07C 51/02* (2006.01)
*C07C 51/43* (2006.01)
*C07C 51/48* (2006.01)

(52) U.S. Cl.
CPC .............. *C07C 51/02* (2013.01); *C07C 51/43* (2013.01); *C07C 51/48* (2013.01)

(58) Field of Classification Search
CPC ......... C07C 51/02; C07C 51/43; C07C 51/48; C07C 55/06
See application file for complete search history.

(56) References Cited

U.S. PATENT DOCUMENTS

| | | | |
|---|---|---|---|
| 1,948,441 A | | 2/1934 | Duus |
| 2,585,616 A | * | 2/1952 | Barnes .................. C23G 1/088 134/3 |
| 3,081,345 A | * | 3/1963 | Carlson ................. C07C 51/275 562/525 |
| 3,519,695 A | * | 7/1970 | Suzuki .................... C07C 17/08 570/241 |
| 3,651,135 A | | 3/1972 | Boichard et al. |
| 8,603,420 B2 | * | 12/2013 | Boiko .................. C01B 7/0706 423/140 |
| 2016/0289075 A1 | * | 10/2016 | Hilakos ................. C01B 25/222 |

FOREIGN PATENT DOCUMENTS

| | | | |
|---|---|---|---|
| CN | 103922416 | * | 7/2014 |
| DE | 1014095 B | | 8/1957 |
| SU | 476249 A1 | | 7/1975 |
| SU | 655656 A1 | | 4/1979 |
| SU | 945246 A1 | | 7/1982 |

OTHER PUBLICATIONS

CN103922416 translated (Year: 2014).*
Bullough et al. (The Solubility of Ferrous Sulphate in Aqueous Solutions of Sulphuric Acid, J. appl. Chem., pp. 703-707, Published Dec. 1952) (Year: 1952).*
Parchem (Ferrous Sulfate Monohydrate supplier distributor, pp. 1-7, Published Jan. 2010) (Year: 2010).*
International Search Report for PCT/IL2017/051021, dated Nov. 29, 2017, 3 pages.
Written Opinion of the International Searching Authority for PCT/IL2017/051021, dated Nov. 29, 2017, 4 pages.

* cited by examiner

*Primary Examiner* — Jafar F Parsa
*Assistant Examiner* — Blaine G Doletski
(74) *Attorney, Agent, or Firm* — Roach, Brown, McCarthy & Gruber, P.C.; Kevin D. McCarthy

(57) ABSTRACT

The invention provides a process for recovering oxalic acid used in ferrous metal pickling procedures, thereby reducing the total cost and environmental load of the pickling treatments.

9 Claims, 1 Drawing Sheet

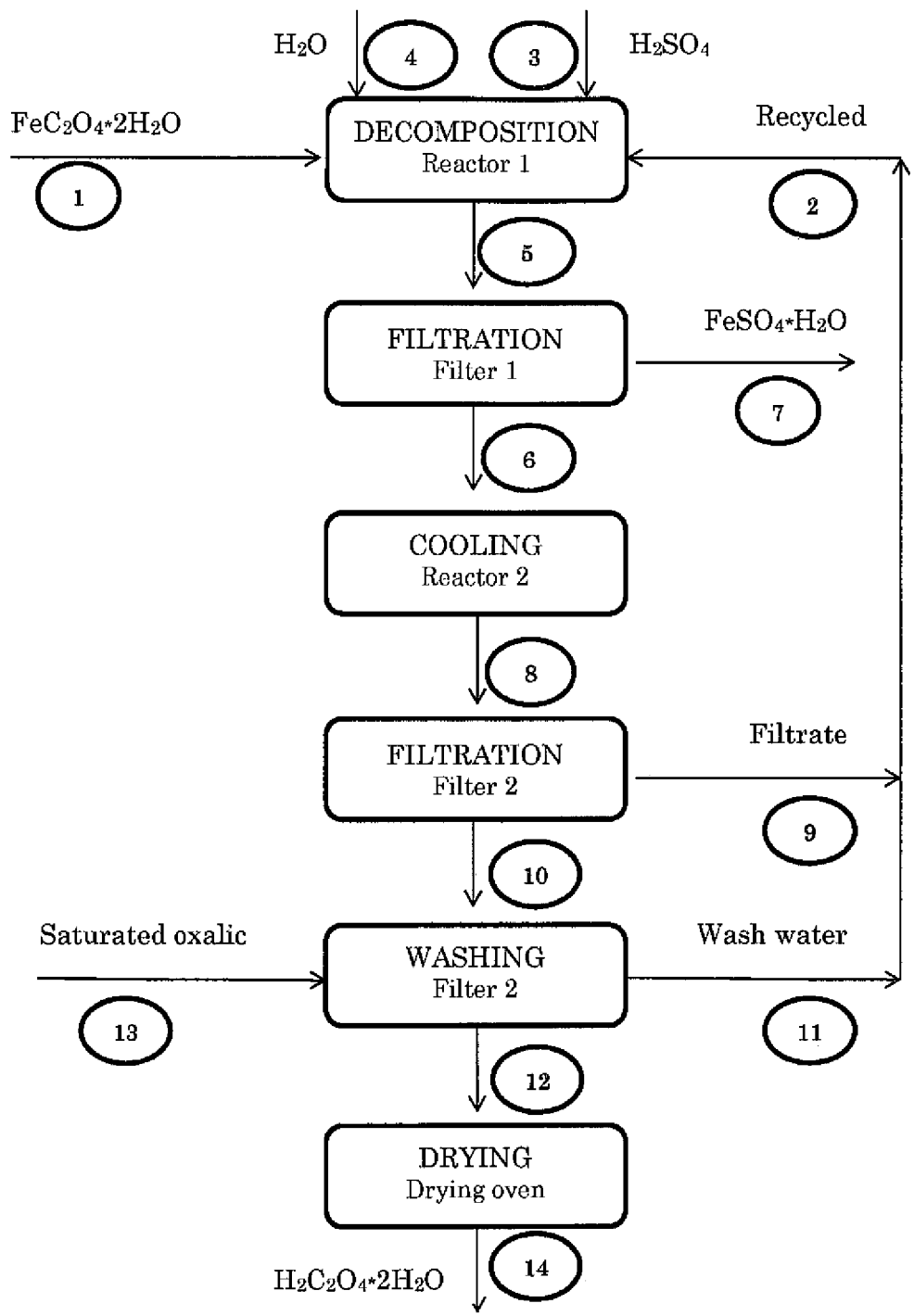
*FLOW DIAGRAM OF OXALIC ACID RECOVERY FROM FERROUS OXALATE DIHYDRATE*

RECOVERY OF OXALIC ACID FROM INDUSTRIAL FERROUS OXALATE

FIELD OF THE INVENTION

The present invention relates to the environmentally "green" galvanization process, in particular to the regeneration of the iron recovering component—oxalic acid—used for renewing pickle liquor after ferrous metal cleaning. The quality of produced oxalic acid allows for its use also in other sectors of industry.

BACKGROUND OF THE INVENTION

Oxalic acid is used as an iron-precipitating agent in the formulations for the regeneration and recycling of pickling acids, including hydrochloric, sulfuric, phosphoric, acetic, and nitric. The present inventors described a process of recycling spent pickling acids, providing processing ferrous oxalate into marketable iron oxide product (U.S. Pat. No. 8,603,420). The present invention relates to recovering oxalic acid from ferrous oxalate, aiming at decreasing the cost of the regeneration of the acids in the ferrous metal pickling.

Oxalate recovery is described in several publications. Mostly, ferric oxalate solution is involved, which reacts with calcium chloride, producing solid calcium oxalate to be separated from slurry by filtration. Calcium oxalate then reacts with sulfuric acid to provide soluble oxalic acid and a precipitate of gypsum as a byproduct (for example, SU 655656, SU 945246). In another attitude, ferric cations are firstly reduced, followed by recovering ferrous oxalate and regenerating oxalic acid by sulfuric acid (Hilakos S.: Jacobs' New Process for Removing Iron from Phosphoric Acid, 39th Annual Clearwater Conference, Jun. 5-6, 2015). It is an object of this invention to provide a method for recovering oxalic acid after its use in ferrous metals pickling procedures.

It is another object of this invention to provide an industrially applicable process for recycling oxalic acid used in surface treatments of ferrous metals, the process being cost effective and presenting a minimum load on the environment.

Other objects and advantages of present invention will appear as the description proceeds.

SUMMARY OF THE INVENTION

The invention provides a process for recovering oxalic acid from ferrous oxalate obtained in ferrous metal pickling industrial procedures, comprising i) providing a water based slurry of said ferrous oxalate in an acid resistant, stirred, and temperature controlled reactor; ii) admixing concentrated sulfuric acid in a predetermined amount to said slurry of step i, under stirring, and allowing to react the reaction mixture for a sufficient reaction time, thereby obtaining a suspension of oxalic acid solution and solid ferrous sulfate monohydrate, whereas the temperature of the reaction mixture increases due to the released heat; iii) filtering said suspension of step ii, thereby separating ferrous sulfate monohydrate from the filtrate of said oxalic acid solution; iv) cooling and stirring said filtrate, thereby crystallizing oxalic acid from said solution and precipitating it; and v) separating, washing, and drying the precipitated oxalic acid. The sulfuric acid may be added in one portion, for example during 10-15 minutes. The process of the invention includes calculating the amount of sulfuric acid to be admixed in said step ii, so that said predetermined amount corresponds to a weight ratio between said added sulfuric acid and said ferrous oxalate (as ferrous oxalate dihydrate) of between 3.5 and 5, such as between 3.6 and 4.8. The total amount of the added sulfuric acid corresponds to between 40 and 55 wt %, such as between 44 and 51 wt % when calculated from the total weight of the added sulfuric acid and the total weight of the reaction mixture.

The released heat warms the reaction mixture up to between 50 and 90° C. The temperature of the reaction mixture may be regulated, if desired, by an aeration of the reactor, or by means of cooling and heating elements. The temperature is preferably between 60 and 70° C. The reaction time is usually between 20 and 60 minutes, such as between 35 and 45 minutes.

In a preferred embodiment, the process of the invention, comprises cooling the filtrate of oxalic acid to a temperature between 5 and 15° C., preferably between 8 and 10° C.; separating the precipitated oxalic acid by filtration and washing it on filter with water saturated by oxalic acid; and drying the washed oxalic acid at a temperature between 50 and 80° C., preferably between 55 and 70° C. The process of the invention preferably utilizes sulfuric acid and oxalic acid in the filtrates obtained during separating and washing oxalic acid for preparing a reaction mixture for another batch according to the instant process, thereby increasing the overall yield; said filtrates may be added to the reaction mixture or they may be used in preparing the reactants.

The process of the invention provides recovered oxalic acid having a purity of at least 99.6%, such as at least 99.7%, for example at least 99.8%, or at least 99.9% such as 99.95%. The recovery yield is typically at least 70%, for example 75% or more; the yield, particularly when reusing the filtrates in following batches, is usually higher, such as at least 80%, for example at least 85%, or at least 90%, or at least 95%.

BRIEF DESCRIPTION OF THE FIGURES

The above and other characteristics and advantages of the invention will be more readily apparent through the following examples, and with reference to the appended FIGURE, wherein:

The FIG. 1 is a flow diagram of the process according to one embodiment of the invention.

DETAILED DESCRIPTION OF THE INVENTION

The invention provides a method for regenerating oxalic acid from ferrous oxalate cake, produced in industrial ferrous metal pickling. The oxalate is decomposed by dissolving in sulfuric acid, followed by separating the produced ferrous sulfate monohydrate by filtration, crystallizing oxalic acid by filtrate cooling, washing and drying the produced oxalic acid, and recycling the filtrate of sulfuric acid. The method comprises a replacement reaction in a slurry, during which ferrous cation passes from the solid ferrous oxalate to the solid ferrous sulfate, while oxalic anion is released from the oxalate solid to the oxalic acid solution.

In accordance with one aspect of this invention, there is provided a method for recovering oxalic acid from dry or wet, washed ferrous oxalate cake, produced as a result of pickle solution regeneration. The method employs water and concentrated sulfuric acid. The ferrous oxalate is resuspended in water in an acid resistant reactor and then reacted with concentrated sulfuric acid added in a precalculated amount, so that its concentration in the reactor will be 40-55% before the reaction starts. The chemical reaction is:

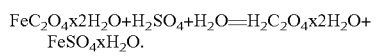
$$FeC_2O_4 \cdot 2H_2O + H_2SO_4 + H_2O = H_2C_2O_4 \cdot 2H_2O + FeSO_4 \cdot xH_2O.$$

The temperature in the reactor usually increases up to 80-90° C. In the reaction, divalent iron of oxalate forms iron sulfate monohydrate, freeing oxalic acid. After complete reaction the slurry of ferrous sulfate monohydrate is produced as a solid, and the solution contains oxalic acid and non-reacted sulfuric acid. The solid is separated by filtration and the filtrate is cooled to 6-15° C. As a result of cooling, the oxalic acid is precipitated and then it is separated from the mixture by filtration. The oxalic acid precipitate is washed and dried, and it can be used for pickle acid regeneration or for other industrial applications. The ferrous sulfate monohydrate can be collected and marketed. Non-reacted sulfuric acid and washing water may be reused in the next batch for ferrous oxalate dissolution. The scheme of the process is provided in the FIG. 1.

In accordance with one aspect of this invention, there is provided an environmentally friendly method for recovering oxalate from ferrous oxalate dihydrate, characterized by employing essentially only one reagent, concentrated sulfuric acid, and by producing two useful marketable products—dry oxalic acid and ferrous sulfate monohydrate. Relating to the FIG. 1, at the first step of the method according to the invention, ferrous oxalate (1) is resuspended in water (4) with stirring inside the acid resistant reactor (Reactor 1). After complete resuspending, concentrated sulfuric acid (3) is added into the reactor, calculated to make 40-55% solution and to provide a weight ratio sulfuric acid/iron oxalate dehydrate of 3.5-5.0, preferably 3.6-4.8. Iron oxalate decomposition starts immediately, heating the slurry; while stirring the mixture, the reaction is complete in 30-60 min, usually 40-45 min. The hot slurry of produced ferrous sulfate monohydrate (5) is pumped to the acid resistant Filter 1 to separate solid ferrous sulfate monohydrate (7) and filtrate (6). The hot (45-90° C., such as 45-60° C.) filtrate (6) is pumped into the acid resistant stirred Reactor 2 for cooling to 5-15° C., preferably 6-10° C. The oxalic acid is precipitated as small (0.2-0.5 mm) crystals and it forms slurry (8) which is pumped to the acid resistant Filter 2 for the separation of retained oxalic acid (10) and filtrate (9), wherein the retained oxalic acid is washed on Filter 2, while having a temperature of 5-15° C., preferably 8-10° C., with water saturated with oxalic acid (13). Filtrate (9) and wash water (11) are pumped into Reactor 1, as a recycled solution (2), for the next batch preparation. Washed cake of oxalic acid (12) goes to the drying oven and it is dried at 50-80° C., preferably 55-60° C., to obtain a product of oxalic acid (14). For the next (second) batch, the mixture comprises a new portion of ferrous oxalate dihydrate (1), recycled solution (2) containing non-reacted sulfuric acid with residues of oxalic acid (9), wash water (11) containing sulfuric acid and a small amount of oxalic acid, clean water (4), and concentrated sulfuric acid (3) calculated to make 40-55% solution as described above, at a weight ratio of sulfuric acid/ferrous oxalate dihydrate of between 3.5 and 5.0, preferably between 3.6 and 4.8. The next batches are repeated as described for the second batch. Products of the process according to the invention are pure oxalic acid and acidic ferrous sulfate monohydrate. The ferrous sulfate can be purified by dissolving in water, filtering and crystallizing as pure ferrous sulfate heptahydrate. The method of the invention provides oxalic acid and a side product of ferrous sulfate for various industrial applications in a completely closed, "green" system. The method according to the invention enables oxalic acid regeneration from industrial ferrous oxalate, produced during the time of different processes including pickling liquors recycling.

The oxalic acid based solid formulations for iron recovery from pickling liquor allow the regeneration of spent pickle acids; the divalent iron is recovered as a solid material—ferrous oxalate. The invention provides means for improving the overall economy, as well as the environmental impact of the involved industrial procedures. This method vastly decreases the expenses of the pickling process by reducing the cost of oxalic acid. The quality of the recovered oxalic acid allows its use also in other industrial applications.

The invention will be further described and illustrated by the following examples.

EXAMPLES

Example 1

242 g of washed and dried ferrous oxalate dehydrate was suspended in 846 g of deionized water in a 2 liters glass reactor with stirring at 1500 rpm at ambient temperature during 30 min. After suspending the oxalate, 1154 g of concentrated sulfuric acid was added into the reactor. The temperature inside the reactor increased from ambient to 80° C. The mixture was stirred for 30 min and then the temperature was allowed to decrease to 65° C. The color of the mixture changed from bright yellow to grayish white as a result of the transformation of ferrous oxalate to ferrous sulfate monohydrate. The produced hot slurry of ferrous sulfate monohydrate was then filtered on a vacuum-filter, and the filtrate was transferred into another 2 liter glass reactor with a stirrer and cooling system. The quantity of ferrous sulfate monohydrate wet cake was 365 g, the volume of the filtrate was 1400 ml and its density at 65° C. was 1.34 g/cc. The hot (50° C.) filtrate inside the glass reactor was stirred and cooled to 10° C. with stirring at 1250 rpm. As a result of cooling, oxalic acid precipitated as sugar-like crystals. The cooling duration was 2 hr. The produced oxalic acid slurry was filtered on a vacuum filter. The weight of produced wet cake of oxalic acid was 120.6 g. The produced cake of oxalic acid was washed by 200 ml water saturated by oxalic acid, and cooled to 10° C. to remove sulfuric acid without losing oxalic acid. The weight of washed and dried oxalic acid was 115.4 g. The filtrate after oxalic acid separation contained 47.18% of sulfuric acid and 1.5 g/l of $Fe^{2+}$. The filtrate volume was 1300 ml and its density was 1.392 g/cc at ambient temperature. This filtrate was collected in a 10 liters glass vessel. The same procedure was repeated two more times. As a result there were collected: 1,000 g of non-washed dry ferrous sulfate monohydrate, 352 g of dry clean oxalic acid, 4,000 ml of the last filtrate and 590 ml of washing water. The produced oxalic acid purity was 99.8% tested by 0.1N NaOH titration. The oxalate recovery from the ferrous oxalate as clean dry powder was 70%. The last filtrate and washing water were used in the next Example 2.

Example 2

242 g of dry washed ferrous oxalate was suspended in a 2 liters glass reactor in 1680 ml of filtrate collected after three cycles in Example 1, containing 47.2% of sulfuric acid at ambient temperature. Resuspending was the same as in Example 1. Then 129 g of concentrated sulfuric acid was added into the reactor with oxalate slurry. As a result of an exothermic reaction the temperature increased to 75° C. Duration of the reaction was 40 min. The color of the slurry changed from yellow to grayish white. Produced ferrous sulfate monohydrate was separated on a vacuum-filter. The weight of wet cake was 262 g. The filtrate quantity was 1200 ml and its density was 1.398 g/cc at a temperature of 60° C. This filtrate was transferred into a 2 liters glass reactor with a stirrer and cooling system. The cooling duration, to reach 10° C. with stirring at 1200 rpm, was 2 hr. As a result of the cooling, oxalic acid precipitated as sugar-like crystals. The oxalic acid slurry was filtered and washed as described in Example 1. The wet cake of produced oxalic acid weighed 185 g and the dry cake weighed 148 g. The oxalate recovery from ferrous oxalate was 87.6%. The oxalic acid purity was 99.9% tested by 0.1N NaOH titration. All products were collected as described in Example 1. The last filtrate quantity was 1060 ml, sulfuric acid concentration was 46.30%, its density at ambient temperature was 1.405 g/cc, and the concentration of $Fe^{2+}$ was 2 g/l.

Example 3

242 g of dry washed ferrous oxalate was resuspended in 156.5 g of deionized water mixed with the last filtrates from Examples 1 and 2. Duration of resuspension was 60 min. The sulfuric acid concentration in the filtrate was 46.3% and the quantity was 1480 ml. After suspending oxalate at ambient temperature, 363.5 g of concentrated sulfuric acid was added into the reactor. As a result, the temperature increased to 85° C. The reaction duration was 60 min. Ferrous sulfate monohydrate was produced, and the mixture was slightly cooled to 70° C. The produced slurry was filtered as described above in Examples 1 and 2. Produced were: wet cake of ferrous sulfate monohydrate 260 g, and filtrate 1,230 ml with a density of 1.398 g/cc at 65° C. The produced filtrate was transferred into a 2 liters glass reactor with a cooling system and stirrer. The cooling duration was 2.5 hr. As a result of the cooling to 10° C., the oxalic acid precipitated as sugar-like crystals. The produced oxalic acid slurry was filtered on a vacuum filter and the cake was washed as described above in Examples 1 and 2. The produced oxalic acid cake was dried at 65° C. during 2.5 hr. The weight of dry oxalic acid was 158 g. The oxalate recovery from ferrous oxalate was 93.5%. The oxalic acid purity was 99.8%, tested by 0.1N NaOH titration. All products were collected as described in Examples 1 and 2. The quantity of filtrate was 1230 ml, and its density was 1.415 g/cc.

While the invention has been described using some specific examples, many modifications and variations are possible. It is therefore understood that the invention is not intended to be limited in any way, other than by the scope of the appended claims.

The invention claimed is:
1. A process for ferrous metal pickling including regeneration of iron-recovering component, comprising steps of:
   i) adding oxalic acid into pickling liquor as an iron-recovering component, thereby precipitating iron from said liquor in the form of ferrous oxalate dihydrate, and providing a water based slurry of said ferrous oxalate dihydrate in an acid resistant, stirred, and temperature controlled reactor;
   ii) admixing concentrated sulfuric acid to said slurry of step i, under stirring, in an amount corresponding to a weight ratio between sulfuric acid and said ferrous oxalate dihydrate of between 3.5 and 5, and allowing to react the reaction mixture for a sufficient reaction time, thereby obtaining a suspension of oxalic acid solution and solid ferrous sulfate monohydrate, whereas the temperature of the reaction mixture increases due to the reaction heat to a temperature of between 50 and 90° C.;
   iii) filtering said suspension of step ii, thereby separating ferrous sulfate monohydrate from the filtrate of said oxalic acid solution;
   iv) cooling said filtrate to a temperature between 8 and 10° C. and stirring, thereby crystallizing oxalic acid from said solution and precipitating said oxalic acid; and
   v) separating the precipitated oxalic acid by filtration and washing said oxalic acid on filter with water saturated by oxalic acid;
   thereby recovering at least 70% of said oxalic acid to be repeatedly used as the iron-recovering component in said metal pickling process, which is a part of an environmentally sustainable galvanization process.

2. The process of claim 1, wherein the total amount of the added sulfuric acid corresponds to between 40 and 55 wt % of said reaction mixture.

3. The process of claim 1, wherein said weight ratio is between 3.6 and 4.8.

4. The process of claim 1, wherein said temperature of the reaction mixture increases to a temperature of between 60 and 70° C.

5. The process of claim 1, wherein said reaction time is between 20 and 60 minutes.

6. The process of claim 1, wherein said reaction time is between 35 and 45 minutes.

7. The process of claim 1, wherein the filtrates obtained during separating and washing oxalic acid in step b) are employed in preparing a reaction mixture for another batch according to the process of claim 1, thereby utilizing non-reacted sulfuric acid and non-filtered oxalic acid for increasing the overall yield and sustainability of said pickling process and said galvanization process.

8. The process of claim 1, wherein the purity of the recovered oxalic acid is at least 99.7%.

9. The process of claim 1, wherein the purity of the recovered oxalic acid is at least 99.9%, and the recovery yield is at least 90%.

* * * * *